United States Patent [19]

Dvorsky et al.

[11] Patent Number: 4,689,233
[45] Date of Patent: Aug. 25, 1987

[54] CORONARY THERAPEUTIC AGENT IN THE FORM OF SOFT GELATIN CAPSULES

[75] Inventors: Stephan Dvorsky, Binningen; Franz Radivojevich, Zofingen; Hans Joss, Murgenthal, all of Switzerland

[73] Assignee: Siegfried Aktiengesellschaft, Zofingen, Switzerland

[21] Appl. No.: 816,253

[22] Filed: Jan. 6, 1986

[51] Int. Cl.$^4$ .......................... A61K 9/48; A61K 9/66
[52] U.S. Cl. ........................ 424/455; 424/80; 424/456; 514/356; 514/962
[58] Field of Search ............ 424/455, 80, 456; 514/356, 962

[56] References Cited

U.S. PATENT DOCUMENTS

| | | | |
|---|---|---|---|
| 1,023,499 | 4/1912 | Bell | 604/310 |
| 1,434,531 | 11/1922 | Cyrenius | 604/197 |
| 1,978,217 | 10/1934 | Muckerjee | 128/272 |
| 3,485,847 | 12/1969 | Bossert et al. | 260/295.5 |
| 3,488,359 | 1/1970 | Bossert et al. | 260/295.5 |
| 3,536,074 | 10/1970 | Aufhauser | 128/222 |
| 3,544,627 | 12/1970 | Carr et al. | 260/544 |
| 3,647,807 | 3/1972 | Bossert et al. | 260/295.5 R |
| 3,784,684 | 1/1984 | Bossert et al. | 424/37 |
| 4,412,986 | 11/1983 | Kawata et al. | 424/80 |

OTHER PUBLICATIONS

Dvorsky et al, CA 104:136082b, (1986) of EPO 143857, Jun. 12, 1985.
Nippon Chemiphar, CA 104:10590x, (1986) of JP 60,105,611, Jun. 11, 1985.
Nippon Chemiphar, CA 99:128364h, (1983) of JP 58,105,913, Jun. 24, 1983.

Primary Examiner—Shep K. Rose
Attorney, Agent, or Firm—Staas & Halsey

[57] ABSTRACT

The present invention relates to a coronary therapeutic agent in the form of soft gelatin capsules, which contain the active substance nifedipine in an organic solvent. In the prior art, there where problems regarding the capsule size and with respect to the low nifedipine active substance concentration. These problems are obviated by the invention, in that nifedipine with PVP, optionally as a coprecipitate and without glycerin, is dissolved in THFP and consequently permits a capsule weight of in all only e.g. 162 mg.

6 Claims, No Drawings

CORONARY THERAPEUTIC AGENT IN THE FORM OF SOFT GELATIN CAPSULES

BACKGROUND OF THE INVENTION

The present invention relates to a coronary therapeutic agent in the form of soft gelatin capsules with glycerin and at least one or more dyes in the capsule shell, which roughly absorbs the wavelength range in which the active substance is sensitive, as well as an opaquing agent and a capsule filling comprising the active substance nifedipine (4-(2-nitrophenyl)-2,6-dimethyl-3,5-dicarbomethoxy-1,4-dihydro-pyridine), as well as an organic solvent for nifedipine and optionally further additives.

Such soft gelatin or biting capsules are described in DE-PS No. 22 09 526. Since, as is known, nifedipine is very difficultly soluble, apart from being highly light sensitive, the coloured or lightproof capsules are undesirably large, because a relatively large quantity of solvents or solubilizers is necessary. This disadvantage is also described in DE-OS No. 28 22 882, which therefore proposes a nifedipine-containing, solid product composition with smaller dimensions. However, apart from the use of polyvinylpyrrolidone, the teaching thereof also requires the use of various celluloses. However, when swallowing, many patients consider such a solid product composition in the form of a tablet to be unpleasant DE-OS No. 31 42 853 also describes solid pharmaceutical products with nifedipine and processes for the preparation thereof. Reference is more particularly made therein to the disadvantages when using the nifedipine-PVP coprecipitate, particularly referring to the widely varying active substance contents in the individual tablets or capsules. According to the teaching given therein, a uniform active substance content is obtained through the use of a specific mixture of PVP with cellulose, starch and cross-linked, insoluble PVPP.

SUMMARY OF THE INVENTION

The problem of the present invention is to obviate the aforementioned disadvantages and in particular to improve the aforementioned soft gelatin capsules in such a way that they have an acceptable size for oral administration and simultaneously the quantity of the active substance nifedipine is considerably increased, but is still uniformly distributed. It is a further object of the present invention to ensure simple production of the soft gelatin capsule with a minimum number of individual components.

According to the invention, this problem is solved by the soft gelatin capsule characterized in claim 1.

It has surprisingly been found that nifedipine and polyvinylpyrrolidone, which has undesired effects when producing tablets, can be very readily solved in tetrahydrofufuryl-alcohol-polyethylene-glycol ether, so that as a liquid with a high, uniformly distributed active substance or nifedipine content, it is very suitable for a liquid capsule filling for a soft gelatin capsule. Test results have revealed that in the case of the capsule filling according to the invention, there is no need to add glycerin, but the omission thereof does not reduce the optimum bioavailability or the physical characteristics of the capsule. There is also no need to add cellulose or PVPP and the like, because they only unecessarily increase the weight and size of the capsule.

A capsule filling composed according to the invention can therefore have a nifedipine concentration which is increased compared with the prior art by a factor of at least two and optionally up to four.

According to the prior art, in order to obtain an adequately stable, resorbable formulation, it is necessary to use capsule fillings with (based on the active substance weight) at 32 times the quantity of solvent or solvents and adjuvants and the capsule content of commercially available nifedipine biting capsules contains at the most 3% active substance according to the examples disclosed in DE-OS No. 22 09 526. As the desired, i.e. the presently considered optimum nifedipine quantity per dosage unit is 5 to 10 mg, in the case of the higher of the aforementioned dosages, this means a capsule filling, i.e. a total quantity of active substance, solvents and adjuvants of more than 380 mg with a volume of at least 0.36 ml. This leads to the need for choosing a very respectable capsule size of 6 minims (1 minim = approximately 0.06 ml; cf Martindale, The Extra Pharmacopoeia, London 1982, p.xxii), which leads to a total filled capsule weight of more than 600 mg.

However, in the case of the biting capsules according to the invention, the weight ratio between the solvent and adjuvant quantity contained in the capsule filling on the one hand and the active substance quantity on the other can be reduced to such an extent that only a capsule volume of 2 minims is required for a 10 mg active substance content. Thus, the filled capsule weight can drop well below 600 mg and is preferably dropped to even less than 210 mg. The resulting reduction in the external dimensions of the capsule permits much easier oral ingestion for the patients undergoing therapy.

Further advantages and features can be gathered from the following subclaims, which can also have inventive significance.

It has also been found the capsule content according to the invention, due to its higher nifedipine concentration is more resistant to light and temperature than the hitherto known soft gelatin capsules, so that the stability problems encountered in the prior art now no longer appear.

The preparation of the soft capsule according to the invention is more particularly performed in that 1. nifedipine and polyvinylpyrrolidone are dissolved in THFP and
2. the solution is introduced by conventional processes into a soft gelatin capsule shell.

It is obvious that, apart from nifedipine and the aforementioned adjuvants, further conventional formulation aids can be used.

DETAILED DESCRIPTION OF THE INVENTION

Hereinafter examples for the soft gelatin capsules according to the invention are give, the weights given relating to the actual moment of preparation due to the subsequent glycerin migration from the shell into the actual content.

| 5 mg NIFEDIPINE SOFT GELATIN CAPSULES | |
|---|---|
| size: 3 minims, oval (0.12 ml) | |
| composition | |
| 1 soft gelatin capsule contains: | |
| filling | |
| nifedipine | 5.00 mg = 4.46% |
| polyvinylpyrrolidone | 14.98 mg |
| tetrahydrofurfuryl-alcohol-polyethylene-glycol | 92.00 mg |
| shell | |

-continued

| | |
|---|---|
| gelatin | 35.42 mg |
| glycerin (85%) | 8.05 mg |
| sorbitol | 5.90 mg |
| titaniumdioxide | 0.18 mg |
| black iron oxide | 0.07 mg |
| FD + C RED 40 | 0.38 mg |
| preservative/water | 0.35 mg |
| | 162.33 mg |

10 NIFEDIPINE SOFT GELATIN CAPSULES size: 2 minims, oval (0.12 ml)
composition
1. soft gelatin capsule contains:
filling

| | |
|---|---|
| nifedipine | 10.00 mg = 8.93% |
| tetrahydrofurfuryl-alcohol-polyethylene-glycol | 72.00 mg |
| polyvinylpyrrolidone | 29.96 mg |
| shell | |
| gelatin | 35.42 mg |
| glycerin (85%) | 8.05 mg |
| sorbitol | 5.90 mg |
| titaniumdioxide | 0.18 mg |
| black iron oxide | 0.07 mg |
| FD + C RED 40 | 0.38 mg |
| preservative/water | 0.35 mg |
| | 162.31 mg |

A further capsule according to the invention contains:

| | |
|---|---|
| 1. filling | |
| nifedipine | 10.000 mg |
| polyvinylpyrrolidone | 15.000 mg |
| menthol | 0.600 mg |
| tetrahydrofurfuryl-alcohol-polyethylene-glycol ether | 247.400 mg |
| total filling weight | 300.000 mg |
| 2. shell | |
| gelatin | 78.500 mg |
| glycerin | 55.000 mg |
| titaniumdioxide | 0.670 mg |
| black iron oxide | 0.125 mg |
| FD + C RED 40 | 0.310 mg |
| purified water | 5.395 mg |
| total shell weight | 140.000 mg |
| 3. total capsule weight | 440.000 mg |

-continued 4. size and shape: 5 minims, oblong.

The soft gelatin capsules according to examples 1 and 2 of the invention consequently weigh only 162 mg and are therefore only roughly ¼ as large as the known capsules. In addition, the weight percentages for nifedipine of 4.46 and 8.93%, based on the capsule content, reveals a much higher concentration than the prior art in the case of liquid fillings for such soft gelatin capsules. The third example gives a somewhat larger capsule, but which is still 1 minim smaller than the prior art.

What is claimed is:

1. A coronary therapeutic agent in the form of soft gelatin capsules, comprising a capsule shell containing glycerin, one or more dyes with an absorption range including the spectral range leading to the decomposition of the active substance, as well as an opaquing agent, together with a capsule filling containing the active substance nifedipine (4-(2'-nitrophenyl)-2,6-dimethyl-3,5-dicarbomethoxy-1,4-di hydropyridine), as well as an organic solvent for nifedipine wherein the capsule filling contains at least 4% by weight of nifedipine, as well as polyvinylpyrrolidone (PVP), both dissolved in a mixture of polyether alcohols of tetrahydrofurfuryl alcohol (THPP), glycerin solely being present as a capsule shell constituent.

2. A coronary therapeutic agent according to claim 1, wherein the filled capsule weight is max 440 mg.

3. A coronary therapeutic agent according to claim 1, wherein the PVP has a molecular weight of approximately 25,000 to 50,000.

4. A coronary therapeutic agent according to claim 1, wherein the capsule shell contains as the dye a mixture of black and/or red iron oxide.

5. A coronary therapeutic agent according to claim 1, wherein the capsule shell contain titanium dioxide as the opaquing agent.

6. A coronary therapeutic agent according to claim 2, wherein the PVP has a molecular weight of approximately 25,000 to 50,000.

* * * * *